United States Patent
Bibette et al.

(10) Patent No.: US 10,143,650 B2
(45) Date of Patent: Dec. 4, 2018

(54) DISPERSION INTENDED FOR ENCAPSULATING AN ACTIVE PRODUCT AND ASSOCIATED USE

(71) Applicant: CAPSUM, Marseilles (FR)

(72) Inventors: Jérôme Bibette, Paris (FR); Thomas Delmas, Marseilles (FR); Enric Santanach Carreras, Marseilles (FR); Leslie Rolland, Cachan (FR)

(73) Assignee: CAPSUM, Marseilles (FR)

( * ) Notice: Subject to any disclaimer, the term of this patent is extended or adjusted under 35 U.S.C. 154(b) by 0 days.

(21) Appl. No.: 14/383,186

(22) PCT Filed: Mar. 8, 2013

(86) PCT No.: PCT/EP2013/054786
§ 371 (c)(1),
(2) Date: Sep. 5, 2014

(87) PCT Pub. No.: WO2013/132083
PCT Pub. Date: Sep. 12, 2013

(65) Prior Publication Data
US 2015/0030648 A1     Jan. 29, 2015

(30) Foreign Application Priority Data

Mar. 8, 2012   (FR) ................................ 12 52115

(51) Int. Cl.
*A23P 10/30*     (2016.01)
*A61K 9/10*     (2006.01)
(Continued)

(52) U.S. Cl.
CPC ............... *A61K 9/10* (2013.01); *A23P 10/30* (2016.08); *A61K 8/04* (2013.01); *A61K 8/11* (2013.01);
(Continued)

(58) Field of Classification Search
CPC .......... A23L 1/0029; A61K 8/04; A61K 9/10; A61K 8/11; A61K 2800/56;
(Continued)

(56) References Cited

U.S. PATENT DOCUMENTS

| 4,778,688 A * | 10/1988 | Matson ................... B01D 3/322 |
| | | 210/321.89 |
| 5,300,305 A * | 4/1994 | Stapler ..................... A61K 8/11 |
| | | 424/435 |

(Continued)

FOREIGN PATENT DOCUMENTS

| EP | 0525731 A2 * | 2/1993 | ............. A23F 5/243 |
| FR | 2939012 A1 * | 6/2010 | .......... A23L 1/22016 |

(Continued)

OTHER PUBLICATIONS

PVP and more . . . BASF product information Apr. 2009 [downloaded from the website http://www.micronal.de/portal/streamer?fid=539456 on Mar. 21, 2016].*

(Continued)

*Primary Examiner* — Sue X Liu
*Assistant Examiner* — Thor Nielsen
(74) *Attorney, Agent, or Firm* — Pearne & Gordon LLP (57) ABSTRACT

A dispersion including a plurality of bodies dispersed in a continuous phase. Each dispersed body including an internal drop formed with an internal phase miscible with the continuous phase, the internal drop (16) receiving an active product. Each dispersed body including, around the internal drop, a membrane formed with an intermediate phase immiscible with the continuous phase and totally surrounding the internal drop. The ratio R1 of the average thickness (e) of the membrane over the average transverse dimension ($D_c$) of the active volume delimited by the internal drop and the membrane is greater than 0.05, and is advantageously (Continued)

less than 0.5. The ratio R2 of the partition coefficient of the active product between the intermediate phase forming the membrane and the internal phase forming the internal drop over the viscosity of the membrane is less than $1 \text{ s}^{-1} \cdot \text{Pa}^{-1}$.

13 Claims, 4 Drawing Sheets

(51) Int. Cl.
    *A61K 8/04*     (2006.01)
    *A61Q 9/00*     (2006.01)
    *A61K 8/11*     (2006.01)
    *A61Q 19/00*     (2006.01)

(52) U.S. Cl.
    CPC .......... *A61Q 19/00* (2013.01); *A23V 2002/00* (2013.01); *A61K 2800/10* (2013.01); *A61K 2800/56* (2013.01); *A61K 2800/63* (2013.01)

(58) Field of Classification Search
    CPC ............ A61K 2800/10; A61K 2800/63; A61Q 19/00; A23V 2002/00
    See application file for complete search history.

(56) References Cited

U.S. PATENT DOCUMENTS

| | | | | |
|---|---|---|---|---|
| 5,330,835 | A * | 7/1994 | Kikuchi | A23F 5/243 264/4.4 |
| 5,498,420 | A * | 3/1996 | Mentrup | A61K 8/14 424/401 |
| 2011/0230390 | A1 * | 9/2011 | Ouali | A61K 8/11 512/2 |
| 2012/0003285 | A1 * | 1/2012 | Bibette | A23L 1/22016 424/401 |

FOREIGN PATENT DOCUMENTS

| | | | |
|---|---|---|---|
| FR | 2939012 A1 | 6/2010 | |
| FR | 2964017 A1 | 3/2012 | |
| WO | 2010070602 A2 | 6/2010 | |
| WO | WO-2010070602 A2 * | 6/2010 | ............... A61K 8/11 |
| WO | 2012089820 A1 | 7/2012 | |

OTHER PUBLICATIONS

US Department of Agriculture CFNP TAP description of Mineral Oil uses and properties, 2002 [downloaded from the website https://www.ams.usda.gov/sites/default/files/media/Min%20oil%20Technical%20Advisory%20Panel%20Report.pdf on Mar. 21, 2016].*
Teixeira et al., "Structure-property studies on the antioxidant activity of flavonoids present in the diet", Free Radical Bio Med 39: 1099-1108 (2005).*
Methyl_salicylate—PubChem.*
Cetyl pyridinium chloride—PubChem.*
Ross-Murphy, "Structure and rheology of gelatin gels: recent progress", Polymer 33(12): 2622-2627 (1992).*
Ross-Murphy, "Structure and rheology of gelatin gels: recent progress", Polymer 33(12): 2622-2627 (1992) (Year: 1992).*
Pyridinium chloride—PubChem 2017 (Year: 2017).*
Methyl salicylate—PubChem 2017 (Year: 2017).*
Desmodur N100—Jun. 2010 product information sheet (Year: 2010).*
Schwarz and Levy "Viscosity changes of sodium alginate solutions after freezing and thawing", J Am Pharm Assoc 46:562-563 (1957) (Year: 1957).*
Lewis and Engelman, "Lipid bilayer thickness varies linearly with acyl chain length in fluid phosphatidylcholine vesicles", J Mol Biol 166(2): 211-217, (1983) (Year: 1983).*
Shinitzky and Barenholz, "Dynamics of the hydrocarbon layer in liposomes of lecithin and sphingomyelin containing dicetylphosphate", J Biol Chem 249: 2652-2657 (1974) (Year: 1974).*
International Search Report for PCT/EP2013/054786 dated Apr. 5, 2013.
Barnes, Howard "Thixotropy—a review" In: Elsevier, XP-002659998, J. Non Newtonian Fluid Mech. 70 (1997) 1-33.

* cited by examiner

DISPERSION INTENDED FOR ENCAPSULATING AN ACTIVE PRODUCT AND ASSOCIATED USE

This application is a National Stage application of PCT international application PCT/EP2013/054786, filed on Mar. 8, 2013 which claims the priority of French Patent Application No. 12 52115 entitled "DISPERSION INTENDED FOR ENCAPSULATING AN ACTIVE PRODUCT AND ASSOCIATED USE", filed with the French Patent Office on Mar. 8, 2012, both of which are incorporated herein by reference in their entirety.

The present invention relates to a dispersion comprising a plurality of dispersed bodies in a continuous phase, each dispersed body including an internal drop formed with an internal phase, the internal drop receiving an active product, each dispersed body including, around the internal drop, a membrane formed with an intermediate phase and totally surrounding the internal drop.

The dispersion according to the invention is intended to encapsulate in a stable way for a significant period of time, for example for more than one week, an active product generally miscible with a continuous phase, with view to its subsequent delivery and/or to its protection against molecules present in the external phase.

The active product is for example a cosmetic active product, a biological active product, or an edible active product.

It is known how to encapsulate molecules which may be unstable within a given medium, in dispersed bodies in the medium, in order to limit the contact with the medium and the molecule before using the molecule. This gives the possibility of preserving the activity of the molecule, while directly delivering it in an adequate medium.

For this purpose, dispersions comprising micron or submicron particles have been designed, for example in the pharmaceutical field, in particular for delivering anticancer agents via a parenteral route.

Such dispersions nevertheless have an encapsulation and retention capability which may be very limited, in particular when the active product to be encapsulated is hydrophilic. Further, the dispersions containing active products may be complex to prepare and to formulate in order to guarantee a satisfactory encapsulation level and stability over time.

An object of the invention is to provide a dispersion which has improved retention and stability properties, notably for hydrophilic active products, and which is nevertheless easy to manufacture.

For this purpose, the object of the invention is a dispersion of the aforementioned type, characterized in that the ratio R1 of the average thickness of the membrane over the average transverse dimension of the active volume delimited by the internal drop and the membrane is greater than 0.05, and is advantageously less than 0.5, and in that the ratio R2 of the partition coefficient of the active product between the intermediate phase forming the membrane and the internal phase forming the internal drop on the viscosity of the membrane is less than $1\ s^{-1} \cdot Pa^{-1}$.

The dispersion according to the invention may comprise one or more of the following features taken individually or according to all technically possible combinations:

- the ratio R1 of the average thickness of the membrane over the average transverse dimension of the active volume is comprised between 0.08 and 0.45, notably between 0.1 and 0.4, and in that the ratio R2 of the partition coefficient of the active product between the membrane and the internal drop over the viscosity of the membrane is less than $0.5\ s^{-1} \cdot Pa^{-1}$, notably less than $0.2\ s^{-1} \cdot Pa^{-1}$;
- the active volume of each dispersed body has an average transverse dimension greater than 0.5 mm, notably comprised between 1 mm and 5 mm;
- the internal drop is formed with an aqueous internal phase, the membrane being formed by an oily intermediate phase;
- the oily phase is formed with an oil selected from the group comprising silicone oils, mineral oils, fatty acid and/or fatty alcohol esters, vegetable oils, and oils compatible with esters such as apolar solvents, mixtures thereof and/or their gelled form;
- the thickness deviation of the membrane over the whole of the external surface of the internal drop is less than 30%;
- each dispersed body includes an external shell surrounding the membrane, the external casing having a thickness of less than that of the membrane;
- the external casing is formed with a gelled polyelectrolyte layer;
- the active product is selected from a cosmetic active product, a biologically active product or an edible active product or mixtures thereof;
- the internal phase is miscible with the continuous phase;
- the intermediate phase is immiscible with the continuous phase.

The object of the invention is also the use of a dispersion as defined above for encapsulating an active product, notably a cosmetic active product for a period of more than one week, advantageously more than one month.

The term "A is miscible with B" generally means that the solubility of A in B is greater than 0.01% by mass. Conversely, the term "A is immiscible with B" means that the solubility of A in B is less than 0.05% by mass.

The invention will be better understood upon reading the description which follows only given as an example and made with reference to the appended drawings, wherein.

Figure 1:
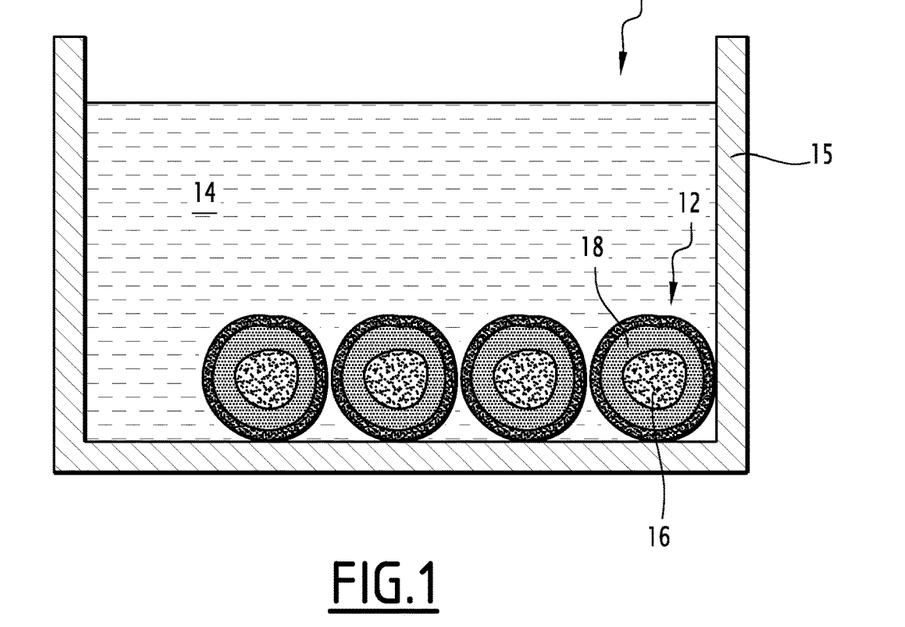
FIG. 1 is a schematic view of a first dispersion according to the invention placed in a first container.

A first dispersion 10 according to the invention is illustrated by FIG. 1. The dispersion 10 comprises a plurality of dispersed bodies 12 and a continuous phase 14 receiving the dispersed bodies 12. The dispersion 10 is received in a container 15.

Figure 2:
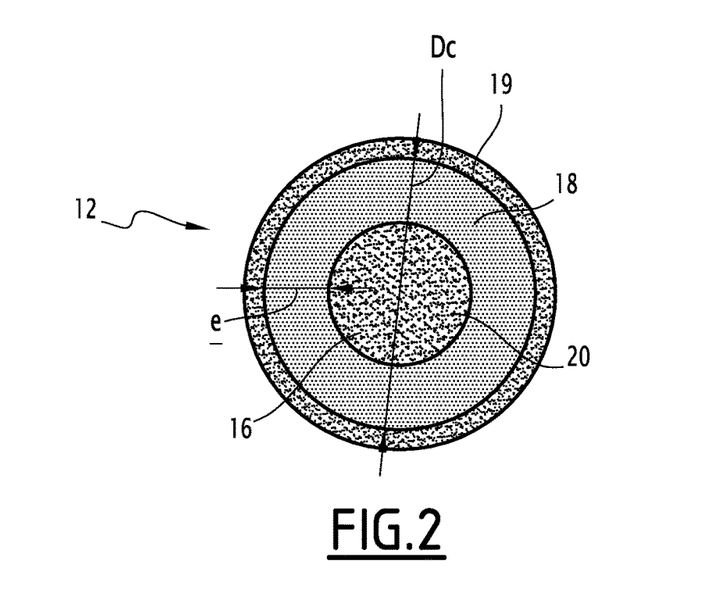
FIG. 2 is enlarged view of an example of a dispersed body encapsulating an active product in a dispersion according to the invention.

As illustrated by FIG. 2, each dispersed body 12 includes an internal drop 16 formed with an internal phase miscible with the continuous phase 14 and a liquid encapsulation membrane 18 formed with an intermediate phase, immiscible with the continuous phase 14.

The internal drop 16 and the membrane 18 form together an active volume.

In the Example illustrated in FIG. 2, each dispersed body 12 advantageously includes an outer casing 19 surrounding the membrane 18 of the dispersed body 12.

According to the invention, the dispersion 10 includes at least one active product 20 received in the internal drop 16, the product 20 being encapsulated in the dispersed body 12.

In an advantageous example, the continuous phase 14 is an aqueous phase. For this purpose, it contains at least 60% by mass of water.

Alternatively, the continuous phase 14 is viscous, it may appear as a gel or a cream with an aqueous base having a viscosity of more than 1,000 mPa·s. This viscosity is generally comprised between 2,000 mPa·s and 20,000 mPa·s, in particular comprised between 4,000 mPa·s and 15,000 mPa·s. These viscosities are measured by the following method:

A viscometer of the Brookfield DV-II type with a mobile (spindle) of size (No.) 05 is used. About 150 g of solution are placed in a beaker with a volume of 250 ml, having a diameter of about 7 cm so that the height of the volume occupied by the 150 g of solution is sufficient for reaching the gauge marked on the mobile.

Next, the viscometer is started with a speed of 10 rpm and one waits for the value displayed on the screen to be stable.

As illustrated by FIG. 2, each dispersed body 12 has a substantially spherical shape. The active volume formed by the internal drop 16 and by the membrane 18 has an average transverse dimension $D_c$, greater than 0.5 mm, and less than 8 mm, preferentially less than 5 mm The dispersed bodies 12 advantageously have a monodispersed distribution. In this respect, size polydispersity of the dispersed bodies 12, as measured by the variation coefficient $C_V$ consisting of the ratio of the standard deviation of the average transverse dimension of the dispersed bodies 12 over the average transverse dimension average of the dispersed bodies 12 is less than 10%, and notably comprised between 1% and 5%.

The average transverse dimensions $D_c$ of each dispersed body 12 and of the active volume, and polydispersity are advantageously measured on at least seven bodies 12 by means of the image processing software package "Image J" on the basis of a photograph of the dispersed bodies 12 taken as a top view with a digital camera.

The area A of each body 12 is determined by means of the software package "Image J" and the average transverse dimension $D_c$ is calculated by considering that the area is a disc with the equation $A=\pi(D_c/2)^2$.

The internal drop 16 is advantageously formed with a phase miscible with the continuous phase 14. In the example illustrated in the figures, the internal drop 16 is formed with an aqueous phase including at least 70% by mass of water.

The internal drop 16 advantageously has a spherical shape. Alternatively, the internal drop 16 has an elliptical or ovoidal shape.

The viscosity of the internal phase 16 is for example less than 50,000 mPa·s and preferably less than 30,000 mPa·s. The core 40 is based on a phase, in majority an aqueous phase, or on the contrary on a phase, in majority an oily phase.

This viscosity is advantageously measured by the method described above.

Alternatively, the internal phase may be gelled with the purpose of suspending therein solid particles (flakes, mother-of-pearls, particles of metal or mineral oxides (silica, carbonates ... )).

The osmotic pressure in the internal drop 16 is substantially equal to the osmotic pressure in the external phase 14.

Thus, the difference in osmotic pressure between the internal drop 16 and the external phase 14 is less than 10% of the osmotic pressure in the internal drop 16. These osmotic pressures are measured by the following method:

An osmometer is used (Cryoscopic Osmometer OSMO-MAT 030 from Gonotec) for measuring the osmotic pressure. A sample of 50 μl of the continuous phase, or a sample of the internal phase extracted from the capsules, is introduced into an Eppendorf container of 1.5 ml. This Eppendorf is triggered on the apparatus. The apparatus then cools the sample until the sample crystallizes. The crystallization temperature value obtained then allows measurement of the osmotic pressure of the sample in osmol/kg.

As indicated above, each internal drop 16 may contain one or several cosmetic, biologically active or edible active products 20.

In an alternative, the internal drop 16 comprises a cosmetic active ingredient such as sodium hyaluronate or other moisturizing/repairing molecules, vitamins, enzymes, anti-wrinkle actives, anti-ageing agents, protective/anti-radical agents, antioxidants, soothing agents, softeners, anti-irritation agents, tensing/smoothing agents, emollients, thickeners, anti-orange peel agents, firming agents, sheathing agents, draining agents, anti-inflammatories, depigmentation agents, bleaches, self-tanning agents, exfoliants, stimulating cell renewal or stimulating skin microcirculation, UV-absorbing or UV-filtering agents, anti-dandruff agents.

The internal drop 16, beyond a simple solution, may for example be a cream, an emulsion, a lotion, a gel or an oil for the skin (hands, face, feet, etc.), a foundation (liquid, solid), a preparation for baths and showers (salts, foams, oils, gels, etc.), a product for hair care (hair dyes and discoloring agents), a cleansing product (lotions, powders, shampoos), a hair care product (lotions, creams, oils), a hair doing product (lotions, lacquers, brillantines), a shaving product (soaps, foams, lotions, etc.), a product intended to be applied on the lips, a sunscreen product, a sunless tanning product, a product for whitening the skin, an anti-wrinkle product.

In an another alternative, the internal drop 16 comprises a biologically active product advantageously selected from anticoagulants, anti-thrombogenic agents, anti-mitotic agents, anti-proliferation agents, anti-adhesion agents, anti-migration agents, cell adhesion promoters, growth factors, anti-parasite molecules, anti-inflammatories, angiogenic agents, angiogenesis inhibitors, vitamins, hormones, proteins, anti-fungal agents, antimicrobial molecules, antiseptics or antibiotics.

Alternatively, the internal drop 16 contains reactive agents such as proteins or reagents intended to form a bioreactor, or form artificial cells for implants.

In another alternative, the internal drop 16 contains an edible product. Edible products intended to be consumed by a human being or by an animal are advantageously vegetable or fruit purees such as mango puree, pear puree, coconut puree, cream of onions, of leeks, of carrots, or other preparations which may mix several pieces of fruit or vegetables. Alternatively, these are oils such as a food oil, of the olive oil, soybean oil, grape seed oil, sunflower oil type, or any other oil extracted from plants.

The internal drop 16 may also comprise excipients, such as thickeners, or flow property modifiers. These thickeners are for example polymers, cross-polymers, microgels, gums or proteins, including polysaccharides, celluloses, polyosides, polymers and co-polymers based on silicone, colloidal particles (silica, clays, latex ... ).

The internal drop 16 is macroscopic. Its volume is advantageously comprised between 1% and 75% of the total volume of the dispersed body 12 and is notably comprised between 1% by volume and 60% by volume of the total volume of the dispersed body 12.

The intermediate membrane 18 is placed around the internal drop 16. The totality of the external surface of the internal drop 16 is covered with the intermediate membrane 18, so that the internal drop 16 does not include any exposed region.

As this was seen above, the intermediate membrane 18 is immiscible with the internal drop 16. Thus, the solubility of the intermediate membrane 18 in the internal drop 16 is less than 0.05% by mass, or even less than 0.02% by mass.

When the continuous phase 14 is aqueous, the membrane 18 is for example formed with one or several oils selected from the group comprising silicone oils, mineral oils, fatty acid and/or fatty alcohol esters, vegetable oils, and oils compatible with esters such as apolar solvents. These oils may be used alone, as a mixture or further in the gelled form.

The intermediate membrane 18 may thus also comprise excipients, such as thickeners, or flow property modifiers. These thickeners are for example polymers, cross-polymers, microgels, gums or proteins, including polysaccharides, celluloses, polyosides, polymers and co-polymers based on silicone, colloidal particles (silica, clays, latex . . . ).

The gelling of a vegetable oil may thus be carried out by means of Creagel Crystal SUN (creation colours) or further Transgel 110PDI (Aiglon). In parallel, the gelling of silicone oil, for example dimethicone, may be carried out by adding a gelling agent of the silicone cross-polymer type, for example KSG 15 or USG107A from Shin Etsu.

The membrane 18 has a substantially constant thickness. Advantageously, the variation of the maximum thickness of the membrane 18 is less than 30% of the average thickness of the membrane 18.

This thickness variation is for example measured by taking six thickness measurements along three perpendicular axes.

The dispersed body 12 thus includes an isotropic structure. This also results from the equilibrium of the osmotic pressure between the outside of the dispersed body 12 and the internal drop 16.

The thickness of the membrane 18 is for example comprised between 0.1 mm and 3 mm, and notably between 0.3 mm and 2 mm.

It advantageously has a suitable viscosity with a threshold stress allowing suspension without any creaming of the internal drop 16 in the membrane 18.

The membrane 18 generally has a viscosity of less than 200,000 mPa·s and notably less than 50,000 mPa·s, advantageously less than 30,000 mPa·s, as measured by the method described earlier.

The membrane 18 is advantageously liquid. In one alternative, the membrane 18 is achieved on the basis of a thixotropic phase, which is in the liquid and de-structured state when it flows (for example during the manufacturing process), but which is substantially solid or gelled at rest.

By "liquid when it flows", is meant that the behavior of the intermediate phase is viscous, i.e. the deformation of the material not only depends on the applied stress but also on the duration during which this stress is applied. A way for characterizing this behavior is with a creep test by means of a rheometer on the sample, a characteristic stress of the applied flows during the manufacturing is applied and the deformation curve versus time is plotted (data obtained with the software of the rheometer). If the curve has a non-zero slope for long times (more than 30 seconds), the intermediate phase may be considered as being liquid. If this slope is zero, the intermediate phase may be considered as being solid.

By "solid or gelled at rest", is meant that the behavior of the solid or gelled intermediate phase at rest, i.e. the deformation of the material, only depends on the applied stress. A way of characterizing this behavior is with a creep test by means of a rheometer, on the sample, a characteristic stress of the ones undergone by the membrane at rest versus time is applied (data obtained with the software of the rheometer). If the curve has a zero slope for long times (more than 30 seconds), the intermediate phase may be considered as being solid. If this slope is non-zero, the intermediate phase may be considered as being liquid.

In one alternative, the membrane 18 may itself also contain active products.

Finally, the whole of the phases used may further contain molecules of cosmetic interest such as actives, coloring agents, stabilizers, preservatives, modifying agents selected from texture, viscosity, pH, osmotic force or refractive index modifying agents.

According to the invention, the ratio R1 of the average thickness e of the membrane 18 over the average transverse dimension $D_c$ of the active volume formed by the internal drop 16 and the membrane 18 is greater than 0.05. This ratio R1 is advantageously comprised between 0.05 and 0.5, preferably between 0.08 and 0.45, and still more preferentially from 0.1 to 0.4.

Moreover, the ratio R2 of the partition coefficient of the active product 20 contained in the internal drop 16, between the liquid membrane 18 and the internal drop 16, over the viscosity of the membrane 18 is less than 1 $s^{-1} \cdot Pa^{-1}$, and is notably less than 0.5, so as to be even more preferentially less than 0.2 $s^{-1} \cdot Pa^{-1}$.

Thus, in a preferential embodiment of the invention, R1 is comprised between 0.05 and 0.5, and R2 is less than 1 $s^{-1} \cdot Pa^{-1}$.

In another advantageous method, R1 is comprised between 0.08 and 0.45, and R2 is less than 0.5 $Pa^{-1} \cdot s^{-1}$.

In still another preferential embodiment, R1 is comprised between 0.1 and 0.4, and R2 is less than 0.2 $Pa^{-1} \cdot s^{-1}$.

The inventors have noticed in a particularly surprising way that the ratios R1 and R2 in the aforementioned ranges led to particularly effective retention of the active product 20 contained in the internal drop 16 by the external membrane 18, while avoiding the risks of leakage through the membrane 18.

The average transverse dimension $D_c$ of the active volume of the dispersed body 12 and the thickness e of the membrane 18 may be determined by the following method.

The samples comprising about ten dispersed bodies 12 are deposited on a plate. A Veho Discovery VMS 001 camera connected to a computer is placed so as to be able to observe the sample from the top, and therefore see the bodies 12 on the plate. The color of the plate will be selected so as to obtain the best contrast between the bodies 12 and the plate.

The acquisition software package used is Astra Image Webcam Video Grabber. A photograph is then recorded in order to be able to measure the area of the active volume of the bodies 12 and the area corresponding to the internal drops of the bodies 12.

The recorded photographs are then utilized with "Image J". The area measurements are obtained in pixels, and then converted into metric units by means of the use of a standard. When considering a spherical shape, it is then possible to determine average values of $D_c$ and e by averaging the values obtained on the whole of the bodies 12 of the characterized sample. For this purpose, the formula: Area (internal volume)=$\Pi*(D_c/2)^2$ and Area (internal gutter)=$\Pi*(d_{internal\ drop}/2)^2$ are used, which allows inference of $D_c$ and $d_{internal\ drop}$. e is calculated with the formula 2 e=$D_c-d_{internal\ drop}$.

The ratio of the partition coefficient $C_p$ of the active product 20 between the membrane 18 and the internal drop 16 is obtained by determining the partition coefficient of this active product 20 between a homologous phase to the intermediate phase forming the membrane 18 and a homologous phase to the internal phase forming the internal drop 16. The ratio $C_p$ is calculated with the following equation:

$C_p$=K=[active in the membrane phase]/[active in the internal phase].

In particular, when the internal drop 16 is aqueous, and when the membrane 18 is oily, the ratio $C_p$ may be estimated by using log P=log K with:

$C_p$=K=[active in octanol]/[active in water].

Log P (a so-called octanol/water partition coefficient of a molecule) gives an estimation of the hydrophobicity of the relevant molecule and has the advantage of being referenced/tabulated and therefore of being easily accessible for most standard molecules. Further, the value of log P (=log (K)) may be simply evaluated by means of easily accessible molecular modeling software packages on the Internet such as for example on www.molispiration.com, www.vcclab.org/lab/alogps/start.html.

Experimental determination is possible with the following method: an accurate amount of the active is weighed and solubilized in one of the two water or octanol phases. Two equivalent volumes of both phases are then put into contact with stirring. The concentrations of the active product in each of both phases are then measured after thermodynamic equilibrium of the system. This concentration measurement may for example be carried out by directly measuring the absorbance, if the molecule absorbs light, or by liquid chromatography. This measurement is for example carried out at 22° C.

The coefficient K is then determined experimentally by the ratio of the concentration of the active in octanol over that in water.

Conversely, when the internal phase forming the internal drop 16 is an oily phase and the intermediate phase forming the liquid membrane is an aqueous phase, the partition coefficient $C_p$ may be estimated by the coefficient log P=log K' with K'=1/K=[active in water]/[active in octanol].

The viscosity η of the membrane 18 is determined by the following method:

In order to measure the viscosity of the membrane, it is possible to extract with a syringe the membrane 18 on several bodies 12, and then of conducting a measurement as described above. Alternatively, the dispersed bodies 12 are mixed and/or destroyed, and the obtained mixture is centrifuged in order to separate the oily phase from the aqueous phase. The (oily or aqueous) phase forming the membrane 18 is then recovered and a measurement of viscosity is conducted as described earlier.

In the case when the membrane 18 is oily, and in the case when the internal drop 16 is aqueous, the coefficient K is generally less than 1, notably less than $10^{-1}$, preferably less than $10^{-2}$ and the viscosity of the membrane 18 is generally comprised between 0.001 Pa·s and 200 Pa·s, preferably between 0.01 Pa·s and 200 Pa·s.

Conversely, in the case when the membrane 18 is aqueous, and the internal drop 16 is oily, the coefficient K' is generally less than 1, notably less than $10^{-1}$, preferably less than $10^{-2}$. The viscosity of the membrane 18 is generally comprised between 0.001 Pa·s and 200 Pa·s, preferably between 0.01 Pa·s and 200 Pa·s.

In a particular embodiment, each dispersed body 12 includes an outer casing 19 made on the basis of a gelled polymer.

The outer casing 19 is advantageously formed with a monolayer of a gelled homogeneous material.

The gelled casing 19 of the bodies 12 comprises a gel containing water and at least one polyelectrolyte which is reactive to multivalent ions. The casing 19 may further contain a surfactant.

By «polyelectrolyte reactive to polyvalent ions», in the sense of the present invention, is meant a polyelectrolyte which may pass from a liquid state in an aqueous solution to a gelled state under the effect of contact with a gelling solution containing multivalent ions such as ions of an earth alkaline metal for example selected from calcium ions, barium ions, magnesium ions.

In the liquid state, the individual polyelectrolyte chains are substantially free to flow relatively to each other. A 2% by mass polyelectrolyte aqueous solution then has a purely viscous behavior at the shear gradients which are characteristic of the shaping process. The viscosity of this solution with zero shearing is between 50 mPa·s and 10,000 mPa·s advantageously between 3,000 mPa·s and 7,000 mPa·s. This viscosity at the characteristic shear gradients of the flows applied during the manufacturing of the bodies 12 is for example measured with a stress or deformation rheometer, imposed at the manufacturing temperature, 25° C. for example. For measurements, a cone-plane geometry will be used with a diameter comprised between 10 and 50 mm, and a cone angle of at most 2°.

The individual polyelectrolyte chains in the liquid state advantageously have a molar mass of more than 65,000 g/moles.

In the gelled state, the individual polyelectrolyte chains form with the multivalent ions, a coherent three-dimensional lattice which retains the liquid core and prevents its flow. The individual chains are retained relatively to each other and cannot freely flow relatively to each other. In this state, the viscosity of the gel formed is infinite. Further, the gel has a flow stress threshold. This stress threshold is greater than 0.05 Pa. The gel also has a non-zero elastic modulus greater than 35 kPa.

The three-dimensional gel of the polyelectrolyte contained in the casing 19 confines the water and the surfactant when it is present. The mass content of the polyelectrolyte in the casing 19 is for example comprised between 0.5% and 5%.

The polyelectrolyte is preferably a harmless biocompatible polymer for the human body. For example it is produced biologically.

Advantageously, it is selected from polysaccharides, synthetic polyelectrolytes based on acrylates (sodium, lithium, potassium or ammonium polyacrylate, or polyacrylamide), synthetic polyelectrolytes based on sulfonates (sodium poly (styrene sulfonate), for example). More particularly, the polyelectrolyte is selected from an earth alkaline alginate, such as sodium alginate or potassium alginate, gellan or a pectin.

The alginates are produced from brown algae called "laminaria", designated by the term of "sea weed".

Such alginates advantageously have an α-L-guluronate content of more than about 50%, preferably more than 55%, or even more than 60%.

The surfactant, when it is present, is advantageously an anionic surfactant, a non-ionic surfactant, a cationic surfactant or a mixture thereof. The molecular mass of the surfactant is comprised between 150 g/mol and 10,000 g/mol, advantageously between 250 g/mol and 1,500 g/mol.

In the case when the surfactant is an anionic surfactant, it is for example selected from an alkylsulfate, an alkyl sulfonate, an alkylarylsulfonate, an alkaline alkylphosphate, a dialkyl sulfosuccinate, an earth alkaline salt of saturated or unsaturated fatty acids. These surfactants advantageously have at least one hydrophobic hydrocarbon chain having a number of carbons of more than 5, or even 10 and at least one hydrophilic anionic group such as a sulfate, a sulfonate or a carboxylate bound to one end of the hydrophobic chain.

In the case when the surfactant is a cationic surfactant, it is for example selected from an alkylpyridium or alkylammonium halide salt such as n-ethyldodecylammonium, bromide or chloride, cetylammonium bromide or chloride (CTAB). These surfactants advantageously have at least one hydrophobic hydrocarbon chain having a number of carbons of more than 5, or even 10 and at least one hydrophilic cationic group, such as a quaternary ammonium cation.

In the case when the surfactant is a non-ionic surfactant, it is for example selected from polyoxyethylene and/or polyoxypropylene derivatives of fatty acids, of fatty alcohols or alkylphenols, arylphenols, or from alkyl glucosides, polysorbates, cocamides.

The mass content of surfactant in the casing is greater than 0.001% and is advantageously greater than 0.1%.

In this example, the casing 19 exclusively consists of polyelectrolyte, of a surfactant when it is present, and of water. The sum of the mass contents of polyelectrolyte, surfactant and water is then equal to 100%.

The casing 19 is thin. For this purpose, the volume ratio $R_v$ of the volume of the core formed by the internal drop 16 and the membrane 18 over the volume of the casing 19 is greater than 2, and is notably greater than 5. This ratio $R_v$ is advantageously less than 50.

The ratio $R_v$ is for example comprised between 5 and 10.

Thus, the thickness of the casing 19 is notably less than 0.3 mm, and is for example comprised between 0.025 mm and 0.1 mm.

As illustrated by FIG. 1, the casing 19 has a specific mechanical strength, notably when it is positioned in a liquid such as water or in a gas.

Thus, the casing 19 allows the body 12 to resist shear and compressional stresses. In particular, the maximum compressional resistance force of the body 12 is advantageously greater than 40 mN, notably greater than 90 mN and may in certain cases be greater than 200 mN, for example comprised between 400 mN and 600 mN.

Thus, for an intermediate phase based on carrageenans, the force is of the order of 50 mN, for an intermediate phase based on sodium hyaluronate, the force may be comprised between 100 and 150 mN, for a vegetable oil, the force may be for example comprised between 150 and 200 mN and for a crosspolymer, the force is comprised between 400 and 600 mN.

This maximum compressional resistance force is noted by the following method.

The body 12 is deposited on precision scales by means of a piston which advances at a controlled speed (of the order of 2 mm/min). The scales are connected to a computer with software which records the mass versus time. The recorded mass increases as the piston gradually compresses the body 12 until the body 12 bursts.

The measured maximum mass is multiplied by the acceleration of gravity, in order to obtain the corresponding force.

As this was seen above, the casing 19 totally covers the intermediate membrane 18. The internal drop 16 and the membrane 18 are totally confined within the casing 19.

The dispersion 10 is for example manufactured by a method as described in French application no. 1061404 of the Applicant. This method is for example applied in an apparatus 30 illustrated in FIG. 3.

Figure 3:
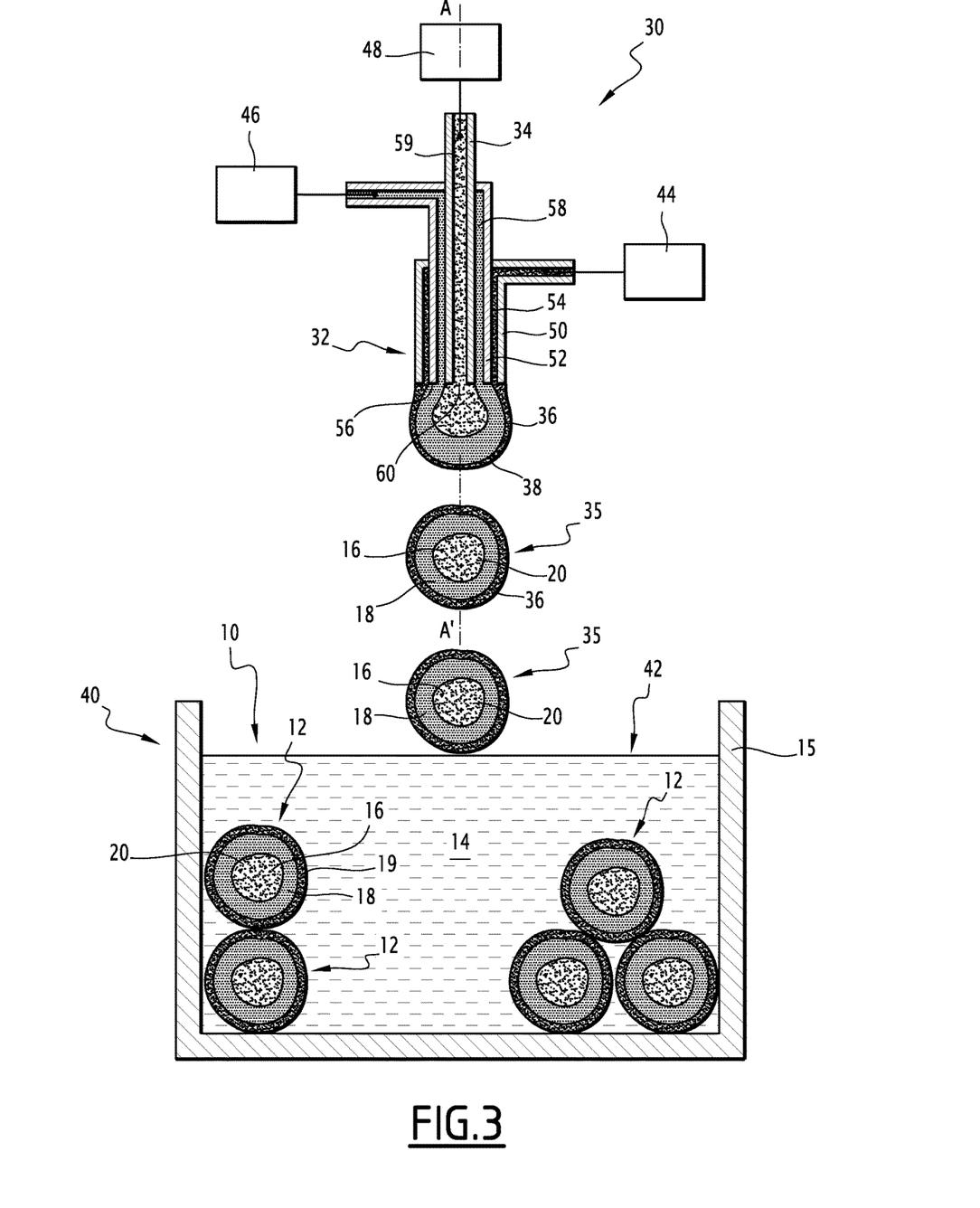
FIG. 3 is a schematic side view taken as a partial sectional view of an example of the device for manufacturing the dispersion, visible in FIG. 1.

As illustrated in this figure, the apparatus 30 comprises an outer jacket 32 and an internal conduit 34 positioned in the jacket 32 in order to co-extrude a series of liquid bodies 35. Each liquid body 35 includes an internal drop 16, a membrane 18 surrounding the internal drop 16, the membrane 18 being coated with a film 36 of a first solution 38 of non-gelled polyelectrolyte intended to form the casing 19 after gelling.

The apparatus 30 further includes an assembly for gelling the film 36, formed in this example by a gelling bath 42, positioned under the jacket 32 away from the latter, and a rinsing and storage bath (not shown).

The apparatus 30 further comprises means 44 for bringing the first solution 38 into the jacket 32, means 46 for bringing an intermediate phase intended to form the membrane 18 into the jacket 32 and means 48 for bringing an internal phase intended to form the internal drop 16 into the internal conduit 34.

In this example, the jacket 32 comprises an outer tube 50 and an intermediate tube 52 positioned coaxially in the outer tube 50. The outer tube 50 and the inner tube 52 delimit together an outer ring-shaped chamber 54 for circulation of the first solution 38. The outer ring-shaped chamber 54 is connected upstream to the means 44 for bringing the first solution.

The outer tube 50 and the inner tube 52 extend along a vertical axis A-A'. They open downwards through an aperture 56 for forming each liquid body 35.

The internal conduit 34 is positioned in the intermediate tube 52. In this example, the internal conduit 34 is coaxially mounted in the tube 52 along the axis A-A'. It defines, with the intermediate tube 52, an intermediate ring-shaped chamber 58 connected upstream to the means 46 for bringing the intermediate phase.

The internal conduit 34 further delimits interiorly a lumen 59 for circulation of the internal phase, connected upstream to the means 48 for bringing the internal phase.

In this example, the lumen 59 of the conduit 34 opens through a downstream aperture 60 for distributing the internal phase which is substantially located at the same level as the aperture 56 for forming drops. Alternatively, this aperture 60 is axially shifted relatively to the aperture 56.

The angle formed by the local axis of the internal conduit 34, taken at the downstream aperture 60 and the internal tube 52, taken at the same aperture, may be comprised between 0° and 90°.

Also, the intermediate ring-shaped chamber 58 advantageously opens at the same level as the aperture 56.

The supply means 44, 46, 48 each include for example a syringe pump, a peristaltic pump or another pressure generating system controlling the flow rate such as for example a pressure pot coupled with a flowmeter and a system for regulating the flow.

A first method for manufacturing a series of bodies 12 for a dispersion 10 according to the invention, applied in the apparatus 30, will now be described.

The method comprises a step for forming at least one internal drop 16 of internal phase in the intermediate phase, and then a step for forming a liquid body 35 consisting of a membrane 18 of intermediate phase containing the internal drop 16. The membrane 18 is coated with a film 36 of a first solution 38 by co-extrusion in the apparatus 30.

The method then comprises a step for having the liquid body 35 fall through a volume of air, and a step for soaking the body 35 in the gelling bath 42, followed by a rinsing/storage step in a rinsing bath.

Initially, the first solution 38 containing polyelectrolyte to be gelled, the solution of intermediate phase, and the solution of internal phase are prepared and are respectively introduced into the means 44 for supplying the first solution 38, into the means 46 for supplying the intermediate phase and into means 48 for supplying the internal phase.

The active product 20 is received in the internal phase.

Depending on the partition coefficient of the active product between the internal phase and the intermediate phase, an intermediate phase with suitable viscosity is selected so that the ratio R2 as defined above is less than $1\ s^{-1} \cdot Pa^{-1}$, or in the ranges defined above.

Next, the means 44, 46, 48 are actuated in order to continuously convey the internal phase in the lumen 59 of the conduit 34, the intermediate phase into the intermediate ring-shaped chamber 58 and the polyelectrolyte solution 38 to be gelled into the outer ring-shaped chamber 54.

In the first method according to the invention, as illustrated by FIG. 1, the internal phase drop 16 present in the intermediate phase is formed at the same time as the intermediate phase membrane 18 covered with the film 36 of solution 38. This simultaneous formation directly occurs at the outlet of the jacket 32, at the aperture 56.

The respective flow rates of internal phase, intermediate phase and polyelectrolyte solution to be gelled are selected according to the respective dimensions of the internal drop 16, of the membrane 18 and of the desired casing 19. In particular, these flow rates are controlled so that the ratio R1 as defined above is greater than 0.05 or in the ranges defined above.

Thus, the relative and independent adjustment of the supplied flow allows adjustment of the thickness of the casing 19, and the relative size of the drop 16 and of the membrane 18.

At the aperture 56, a substantially spherical liquid body 35 consisting of a membrane 18 containing an internal drop 16, the membrane 18 being covered with a solution film 38, is gradually formed.

The film 36 of solution 38 totally surrounds the intermediate drop 20. Further, the polyelectrolyte contained in the solution 38 is maintained in its non-gelled liquid state.

When the weight of the body 35 is greater than the force for retaining it by capillarity on the jacket 32, the body 35 is detached from the jacket 32 and falls into the gelling bath 42 by gravity, through a volume of air. The film 36 of solution to be gelled 38 then comes into contact with the gelling solution contained in the bath 42.

In contact with the multivalent ions from the gelling reagent, the individual polyelectrolyte chains present in the solution 38 connect to each other so as to form a cross-linked lattice which confines the water and optionally the surfactant contained in the solution 38.

A gelled casing 19 as defined above and capable of retaining the membrane 18 and the internal drop 16 is thereby achieved. The casing 19 has a specific mechanical strength, i.e. it is capable of totally surrounding the membrane 18 and of retaining it in order to prevent it from diffusing through the casing 19, even when the body 12 is positioned in a gas such as ambient air.

Next, another body 35 is formed at the lower end of the jacket 32 and the steps described earlier are reproduced for this body 35.

Figure 6:
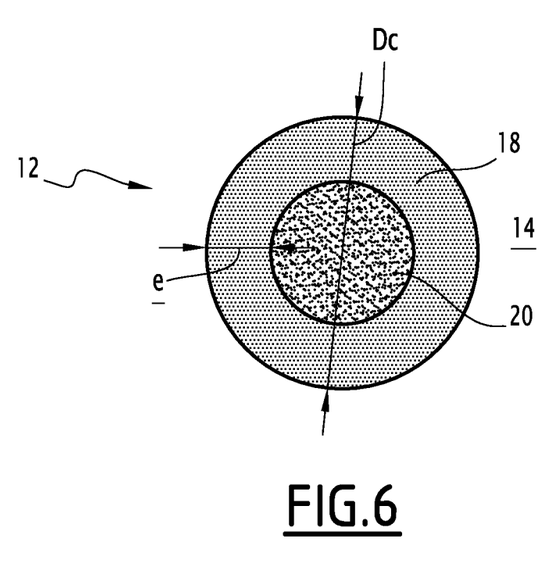
FIG. 6 is a second example of a dispersed body in a dispersion according to the invention.

In an advantageous alternative, illustrated in FIG. 6, each dispersed body 12 is without any outer casing 19. The liquid membrane 18 is directly in contact with the continuous phase 14 in the whole of its outer surface. The internal drop 16 is separated from the continuous phase 14 by the membrane 18.

According to the invention, the ratios R1 and R2 are in the ranges defined above.

In this alternative, the bodies 12 are for example obtained by depolymerization of the outer casing 19, after forming the body 12 as described in the method of FIG. 3.

In one alternative, the continuous phase 14 contains at least one compound which may react with the active product 20 present in the internal drop 16. The membrane 18 thus protects the active product 20 from contact with this compound.

Exemplary embodiments of the dispersion 10 according to the invention will now be illustrated.

In a first example, a dispersed body 12 is manufactured with an aqueous internal drop 16, an oily intermediate membrane 18 so that the ratio R1 is equal to 0.38.

This for example is obtained with a dispersed body 12 including an active volume with an average diameter $D_c$ equal to 4.35 mm and a thickness e of the membrane 18 equal to 1.66 mm. The bodies 12 are dispersed in an aqueous continuous phase 14.

The active product introduced into the internal drop 16 is formed by a dextran polymer having a molecular mass of 2,000 kilodaltons (kDa).

A membrane 18 with a viscosity equal to 23,200 mPa·s (at 10 rpm) and with a thickness of 1.66 mm is formed around the internal drop 16. This membrane 18 is based on a mixture of silicone oil (product KF 96A-6cs (dimethicone) from Shin Etsu) (19% by mass) and of a silicone crosspolymer (product KSG15 from Shin Etsu formed with a mixture of dimethicone, vinyl dimethicone crosspolymer and cyclopentasiloxane) (81% by mass).

The partition coefficient K of the dextran, measured by the ratio of the dextran concentration in octanol over the ratio of the dextran concentration in water is less than $10^{-2}$. R2 is therefore less than $4.31 \times 10^{-4} s^{-1} Pa^{-1}$.

In a second example, a dispersion 10 including dispersed bodies 12 with a structure identical with those of the first example is prepared. However, unlike the dispersion 10 of the first example, the active product is bovine serum albumin. This protein has about 580 amino acids, soluble in a large amount in pure water, with a molecular weight equal to 66.5 kDa.

The partition coefficient $C_p$ of this protein is less than $10^{-3}$. The ratio R2 is then less than $10^4$.

Figure 4:
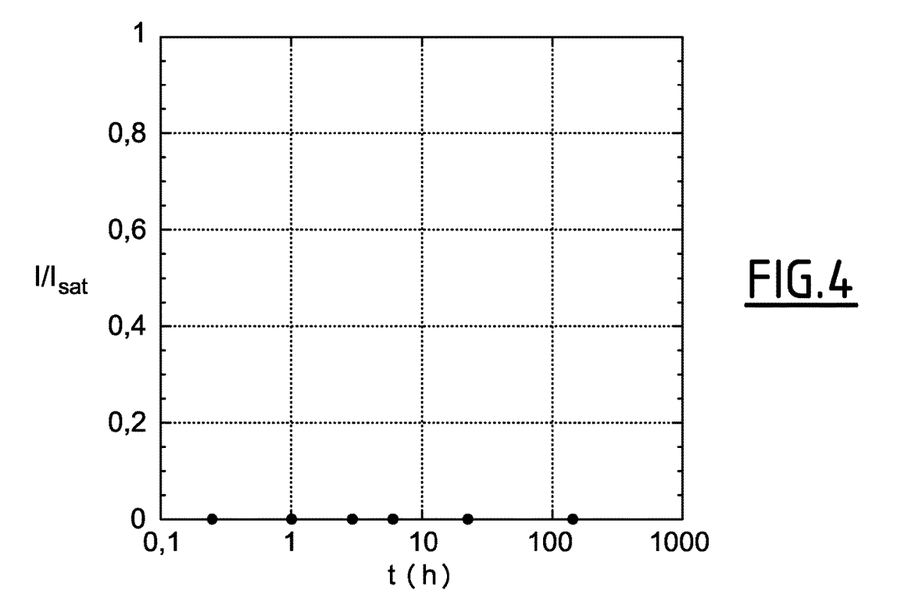
FIG. 4 is a graph illustrating the absorbance in the continuous phase in a dispersion according to the invention, wherein an active absorbent product was encapsulated in the dispersed phase.
Figure 5:
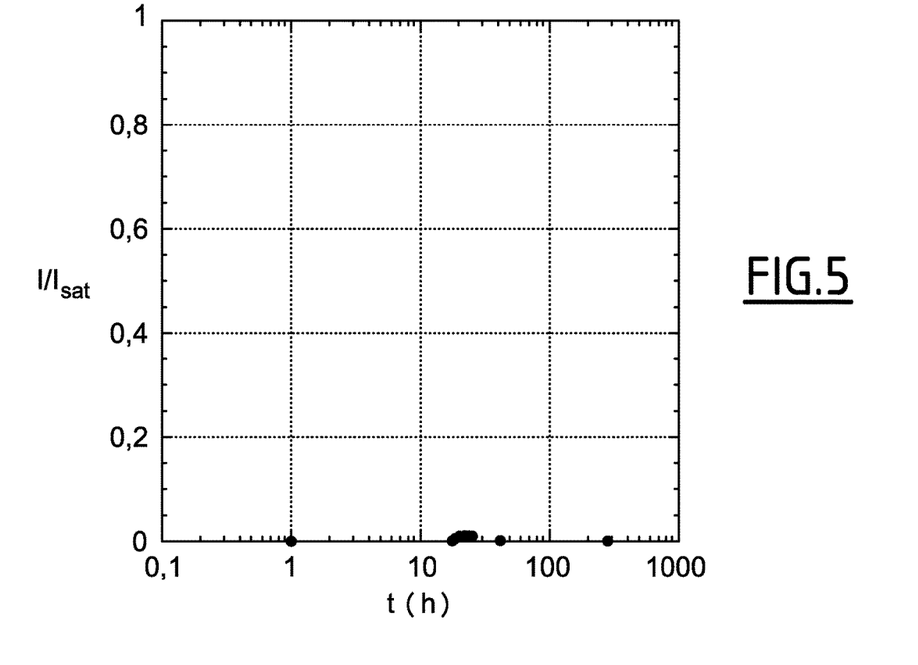
FIG. 5 is a view similar to FIG. 4 for a dispersion according to the invention containing another absorbent active product.

FIGS. 4 and 5 respectively illustrate the ratio of optical absorbance in the continuous phase 14 versus time for respectively the dispersion of the first example containing dextran, and for the dispersion of the second example containing bovine serum albumin. As seen in these figures, no leakage of active product is observed after more than one week at a temperature of 50° C.

Conversely, if the molecule containing each body 12 is Rhodamine B, having a molecular weight equal to 479 g/mol, and a partition coefficient equal to 70.8, the ratio R2 is equal to 3.05 and leakage is observed.

By means of the invention which has just been described, it is therefore possible to have available a dispersion 10 encapsulating in a particularly efficient way active products over time, notably for periods of more than one week or even one month, or even six months at room temperature, for example at 22° C. This encapsulation effect is surprisingly obtained by selecting particularly suitable ratios R1 and R2. The dispersions 10 are simple to make and handle because of the size of the dispersed bodies.

Directly and without any ambiguity, the result of the foregoing is that one skilled in the art is able to carry out the invention from a given active, by determining the expected partition coefficient K of the active between a homologous phase to the intermediate phase intended to form a membrane 18 and a homologous phase to an internal phase intended to form the internal drop 16.

As discussed above, the partition coefficient K is for example determined from the log P coefficient corresponding to the octanol/water partition coefficient of the molecule, which is generally tabulated, with reference to given physico-chemical conditions (for example pH, or temperature), which correspond to those which may be used for manufacturing the dispersed bodies 12.

Alternatively, an experimentation determination as discussed above may be used by one skilled in the art, notably if the physico-chemical conditions for making the dispersed bodies do not correspond to those defined in the tables, if these physico-chemical conditions are capable of giving partition coefficients different from those which are tabulated.

Once the partition coefficient K is determined, one skilled in the art may naturally and without any difficulties select the viscosity required for the membrane 18, in order to obtain a ratio R2 of less than 1 $s^{-1} \cdot Pa^{-1}$. If need be, the viscosity of the intermediate phase intended to form the membrane 18 is adjusted by adding additives modifying the viscosity, which are well known to one skilled in the art.

It directly ensues and without any ambiguity from the foregoing description that the viscosity of the membrane 18 may be determined at the same temperature as the temperature at which is determined the viscosity of the polyelectrolyte intended to form the outer casing 19, i.e. 25° C.

This having been accomplished, the apparatus 30 described above gives the possibility in a known way via the selection of the size of the apertures 56, 60 and of a flow regulation system, of accurately controlling the average thickness of the membrane 18 and the corresponding average transverse dimension of the active volume delimited by the internal drop 16 and by the membrane 18. One skilled in the art is able to carry out the required adjustments in order to obtain bodies 12 having a ratio R1 of more than 0.05.

Moreover, when a mixture of actives has to be placed in a dispersed body 12, one skilled in the art may resort to his/her general knowledge for separating the mixture, for example by chromatography, notably by high pressure liquid chromatography. This gives him/her the possibility of then characterizing the partition coefficient K of each active product of the mixture, as discussed earlier and of thereby adjusting the viscosity of the intermediate phase intended to form a membrane so as to obtain a ratio R2 of less than 1 $s^{-1} \cdot Pa^{-1}$ for each active product of the mixture.

As specified above, the membrane 18 is advantageously liquid or made from a thixotropic phase, without being gelled.

The invention claimed is:

1. A dispersion comprising a plurality of dispersed bodies in a continuous phase, each dispersed body including:
    an internal drop formed with an internal phase, the internal drop receiving an active product,
    around the internal drop, a membrane formed with an intermediate phase and totally surrounding the internal drop, and
    an external casing surrounding the membrane, the external casing formed with a gelled polyelectrolyte layer and having a thickness of less than that of the membrane,
    wherein the ratio R1 of the average thickness of the membrane over the average transverse dimension of the active volume delimited by the internal drop and the membrane is greater than 0.08,
    and wherein the ratio R2 of the partition coefficient of the active product between the intermediate phase forming the membrane and the internal phase forming the internal drop over the viscosity of the membrane is less than 1 $s^{-1}Pa^{-1}$.

2. The dispersion according to claim 1, wherein the thickness deviation of the membrane over the whole outer surface of the internal drop is less than 30%.

3. The dispersion according to claim 1, wherein the ratio R1 of the average thickness of the membrane over the average transverse dimension of the active volume delimited by the internal drop and the membrane is less than 0.45,
    and the ratio R2 of the partition coefficient of the active product between the intermediate phase forming the membrane and the internal phase forming the internal drop over the viscosity of the membrane is less than 0.5 $s^{-1}Pa^{-1}$.

4. The dispersion according to claim 1, wherein the active volume of each dispersed body has an average transverse dimension greater than 0.5 mm.

5. The dispersion according to claim 1, wherein the internal drop is formed by an aqueous internal phase, the membrane being formed by an oily intermediate phase.

6. The dispersion according to claim 5, wherein the oily intermediate phase is formed from an oil selected from the group consisting of silicone oils, mineral oils, fatty acid esters, fatty alcohol esters, vegetable oils, oils compatible with esters, mixtures thereof, and gelled forms thereof.

7. The dispersion according to claim 1, wherein the active product is selected from a cosmetic active product, a biologically active product, an edible active product, or mixtures thereof.

8. The dispersion according to claim 1, wherein the membrane is liquid or is made on the basis of a thixotropic phase.

9. The dispersion according to claim 1, wherein the ratio R1 of the average thickness of the membrane over the average transverse dimension of the active volume delimited by the internal drop and the membrane is less than 0.5.

10. The dispersion according to claim 3, wherein the ratio R1 of the average thickness of the membrane over the average transverse dimension of the active volume delimited by the internal drop and the membrane is comprised between 0.1 and 0.4, and the ratio R2 of the partition coefficient of the active product between the intermediate phase forming the membrane and the internal phase forming the internal drop over the viscosity of the membrane is less than 0.2 $s^{-1}Pa^{-1}$.

11. The dispersion according to claim 4, wherein the active volume of each dispersed body has an average transverse dimension comprised between 1 mm and 5 mm.

12. A method of encapsulating an active product comprising encapsulating the active product in the dispersion of claim 1 to provide the dispersion for a period of more than one week.

13. The method according to claim 12 wherein the period is more than one month.

* * * * *